United States Patent [19]

Holst et al.

[11] 3,965,091

[45] June 22, 1976

[54] PROCESS FOR THE PRODUCTION OF WATER-ADSORBING BUT WATER-INSOLUBLE CELLULOSE ETHERS

[75] Inventors: Arno Holst, Wiesbaden-Biebrich; Helmut Lask, Wiesbaden-Schierstein, both of Germany

[73] Assignee: Hoechst Aktiengesellschaft, Germany

[22] Filed: Nov. 18, 1974

[21] Appl. No.: 524,822

[30] Foreign Application Priority Data
Nov. 22, 1973 Germany.......................... 2358150

[52] U.S. Cl............................ 260/231 A; 260/17 A; 260/231 CM
[51] Int. Cl.$^2$.................. C08B 11/00; C08B 11/20; C08B 11/193; C08B 15/10
[58] Field of Search ...... 260/17 A, 231 A, 231 CM, 260/232

[56] References Cited
UNITED STATES PATENTS

| | | | |
|---|---|---|---|
| 2,517,577 | 8/1950 | Klug et al. | 260/231 CM |
| 2,886,474 | 5/1959 | Kine et al. | 260/17 A |
| 3,029,232 | 4/1962 | Bikales et al. | 260/231 A |
| 3,102,773 | 9/1963 | Needleman | 260/231 A |
| 3,125,406 | 3/1964 | Herman | 260/17 A |
| 3,298,979 | 1/1967 | Hagemeyer et al. | 260/17 A |
| 3,423,163 | 1/1969 | Magat et al. | 260/17 A |
| 3,696,092 | 10/1972 | Tesoro | 260/17 A |

FOREIGN PATENTS OR APPLICATIONS

| | | | |
|---|---|---|---|
| 45-40556 | 12/1970 | Japan | 260/17 A |
| 1,099,239 | 1/1968 | United Kingdom | 260/17 A |

*Primary Examiner*—Ronald W. Griffin
*Attorney, Agent, or Firm*—James E. Bryan

[57] ABSTRACT

This invention relates to an improvement in the process for the production of water-adsorbing, but largely water-insoluble, cellulose ethers, in which cellulose is alkalized in the presence of alkali and isopropanol as a reaction medium and is so reacted with an etherification agent that by etherification only a water-soluble cellulose ether is produced, and in which process a modification agent which is able to react with the still free hydroxyl groups of the cellulose anhydro glucose groups in an alkaline reaction medium is reacted before, during, or after the etherification, the improvement comprising effecting the etherification of cellulose to carboxymethyl cellulose, carboxymethyl hydroxyethyl cellulose, hydroxyethyl cellulose, or methylhydroxyethyl cellulose, reacting with the modification agent in the presence of 0.8 to 7.5 parts by weight of isopropanol, based upon the cellulose weight, and employing a modification agent being one of the formulae

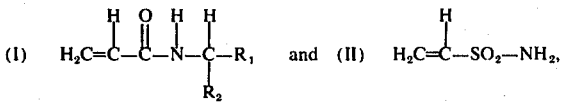

$R_1$ in formula I being hydroxyl, or an acylamino or etherified carbamino group, and $R_2$ in formula I being hydrogen or a carboxyl group.

10 Claims, No Drawings

PROCESS FOR THE PRODUCTION OF WATER-ADSORBING BUT WATER-INSOLUBLE CELLULOSE ETHERS

This invention relates to a process for the production of water-adsorbing, but largely water-insoluble, cellulose ethers.

It is known to cross-link water-soluble carboxymethyl cellulose; which can be produced by etherification of cellulose with monochloroacetic acid, in order to obtain a cellulose ether which is, at least partially, water-insoluble, but which has the capacity of adsorbing relatively large quantities of water and of swelling at the same time. The cross-linking may take place before, after, or simultaneously with, the etherification. Reaction agents which are polyfunctional towards cellulose are used as cross-linking agents, for example epoxy compounds, polychlorinated higher alcohols, or divinyl sulfone. Epichlorohydrin is preferably used, because with it the cross-linking can be carried out simultaneously with the etherification. The cross-linkings take place in the presence of a relatively small quantity of water either in a semi-dry state or in the presence of a relatively large quantity of an inorganic diluent, such as isopropanol, the quantity of which corresponds to a 40-fold quantity of the cellulose. At standard temperature, the reaction of cross-liking requires many hours, e.g. 18; at higher temperature the reaction is more rapid, but even at temperatures above 70°C it still requires several hours, e.g. 3.5.

The object of the present invention is to provide a process for the production of water-adsorbing, but largely water-insoluble (i.e. more than 50 per cent by weight insoluble) cellulose ethers, a process which can be carried out more rapidly.

This object is obtained by proceeding from the known process for the production of water-adsorbing, but water-insoluble cellulose ethers, in which process cellulose is alkalized in the presence of alkali and isopropanol as a reaction medium and reacted with an etherification agent in such a manner that by means of a mere etherification a substantially, i.e. at least 95 per cent by weight, water-insoluble cellulose ether would be produced. The modification takes place before, simultaneously with, or after, the etherification with a reaction agent which is capable of reacting with the still free hydroxyl groups of the cellulose anhydroglucose groups in an alkaline reaction medium. In the course of the etherification of cellulose into carboxymethyl cellulose, carboxymethyl hydroxyethyl cellulose, hydroxyethyl cellulose, or methyl hydroxyethyl cellulose, the modification is performed in the presence of 0.8 to 7.5 parts by weight of isopropanol, based upon the cellulose weight, by means of a modification agent which corresponds to one of the formulae

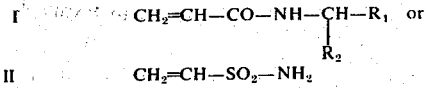

$R_1$ and $R_2$ in formula I being
  $R_1$ an hydroxyl group, or an acylamino or etherified carbamino group and
  $R_2$ is hydrogen or a carboxyl group.

When applying the process to the production of carboxymethyl cellulose or carboxymethyl hydroxyethyl cellulose, the alkalization and etherification as well as the modification are preferably carried out in the presence of 0.85 to 3.0 parts by weight of isopropyl alcohol per part by weight of dry cellulose. When the process is applied to the production of hydroxyethyl cellulose or methyl hydroxyethyl cellulose, the alkalization, etherification, and modification are preferably carried out in the presence of at least 0.85 part by weight, but not more than 7 parts by weight of isopropyl alcohol. In the process it is often most advantageous to use isopropyl alcohol, hereinafter also called isopropanol, in the form of the water-containing product with about 13 per cent by weight of water, which is often used for technical purposes. In the present description, however, isopropyl alcohol or isopropanol are meant to be isopropyl alcohol of 100 per cent concentration, if no other explanation is given.

In order to provide the alkali necessary for the process, aqueous lyes are used in by far most of the cases. During the alkalization, etherification, and modification, the reaction mixture thus contains, apart from the water introduced by the use of 87 per cent isopropanol, water introduced by the lye used. In some cases more water is introduced into the reaction mixtures by the fact that the modification agent is added in the form of an aqueous solution. The entire quantity by weight of water introduced in the reaction mixture, however, should not exceed the quantity by weight of isopropanol present in the mixture. It preferably should be less than two thirds of the quantity by weight of isopropanol.

If in the production of carboxymethyl cellulose or carboxymethyl hydroxyethyl cellulose, the etherification is carried out before the modification, and if this is done in the presence of a substantially higher amount of isopropanol than 3 parts by weight per part by weight of cellulose, it is advisable to remove some of the isopropanol before the modifiction of the cellulose ether takes place, so that it takes place in the presence of about three parts by weight of isopropanol. Otherwise the modification would be less rapid, if the same quantity of cross-linking agent was used.

Of the modification agents, which correspond to the above formula I in which $R_1$ is an acylamino group, those are preferably used in which the acyl group is the formyl group or acetyl group. Of the modification agents, in which $R_1$ is an esterified carbamino group, those are particularly suitable in which the carbamino group is esterified with an aliphatic alcohol group of not more than 5 carbon atoms. The alcohol group may be etherified with a lower alkoxy group, in particular with a methoxy group.

The modification agents used in the process are, for example:
  N-methylol acrylamide
  N-(acrylamido methylene)-acetamide
  N-(acrylamido methylene)-formamide
  N-(acrylamido methylene)-amylurethane
  N-(acrylamido methylene)-methylurethane
  N-(acrylamido carboxy methylene)-ethylurethane
  N-(acrylamido methylene)-methoxy ethylurethane
  vinyl sulfonamide.

Of these agents, up to 100 parts by weight, preferably however less than 25 parts by weight, are employed to 100 parts by weight of cellulose.

The process leads, as do the previously known cross-linking processes, to modified products which contain a certain water-soluble proportion. For many purposes this does not matter, so that a removal of the water-soluble parts is in most cases unnecessary. The effectiveness of the modification agent depends to a certain extent on the intensity with which the mixing is performed during the modification. In the case of intensive mixing, as little as 10 parts by weight of the modification agent per 100 parts by weight of cellulose are sufficient to produce cellulose ethers which adsorb large quantities of water. If a celluloseether is to be obtained which can adsorb large quantities cellulose ether water and if the cellulose ether may contain a relatively large water-soluble portion, i.e. up to 45 per cent by weight, only 5 parts by weight of the modification agent are sufficient for the modification of 100 parts by weight of cellulose ether.

The table below gives the quantity of the portions soluble in pure water at 20°C, i.e. the portions of the modified cellulose ethers given in the examples.

The process requires relatively small quantities of a reaction medium (isopropanol) and, at temperatures of about 50°C, it quickly leads to sufficient modifications, i.e. in about one hour. Products are obtained which have, depending upon the conditions of etherification and modification, different capacities for adsorbing water. Therefore, many different requirements can be met. The capacity for adsorbing water may be extremely high, for example up to a 60-fold weight of the water-insoluble portion of the modified cellulose ether. The adsorbed water is so firmly bonded to the modification product that even a centrifugal force corresponding to a 2,000-fold acceleration of gravity cannot remove it. The table below shows the retention capacity towards pure water at 20°C after the application of such a centrifugal force.

The modified cellulose ethers obtained according to the process may serve various technical purposes, for example as adsorbing materials for medical and hygienic bandages or as dehydrating agents, e.g. for aqueous emulsions.

In the following examples all the percentages are in per cent by weight. The alkalization, etherification, and modification are carried out at the stated temperatures, during kneading and stirring, depending upon the quantity of isopropanol-water reaction medium which is present. The products thus obtained are, if nothing else is stated, neutralized with acetic acid, washed virtually salt-free with 80 per cent methanol, and then dried at 80° to 100°C.

EXAMPLE 1

100 g of cellulose are alkalized in 300 g of 87 per cent aqueous isopropanol with 46 g of 50 per cent soda lye by mixing for 45 minutes at 20°C. Then the thus produced alkali cellulose is modified by adding 50 g of a 48 per cent aqueous solution of N-methylol acrylamide and reacting it at 50°C for 1 hour, while the mixing is continued. Then, the mixture is etherified by adding 55 g of the sodium salt of monochloroacetic acid and by mixing it for one hour at 70°C. Then, it is neutralized, washed, and dried.

The water retention capacity of the modified cellulose ether obtained, in grams of water per 100 g of cellulose ether, as well as its water-soluble portion in per cent by weight, are given in the table below. It also gives the corresponding data for the following examples.

EXAMPLE 2

100 g of cellulose in 670 g of 87 per cent isopropanol are alkalized with 51 g of soda lye (50 per cent) by mixing for 45 minutes at 20°C. Then, the mixture is etherified by adding 61 g of the sodium salt of monochloroacetic acid and further mixing it for 1 hour at 80°C. Then, the mixture is pressed off to a weight ratio of 1 : 3 between solid content and liquid. After adding 30 g of 50 per cent soda lye and 200 g of a 48 per cent aqueous solution of N-methylol acrylamide, the mixture is reacted for 1 hour at 50°C, during constant kneading.

EXAMPLE 3

100 g of cellulose in 670 g of isopropanol (100 per cent) are alkalized in a pressure vessel with 30 g of soda lye dissolved in 189 g of water. The alkalization is carried out for 30 minutes at 20°C, while the material is stirred. Then, the material is modified by adding 50 g of a 48 per cent aqueous solution of N-methylol acrylamide in the course of one hour at 50°C, while the stirring is continued. Then 75 ml of ethylene oxide are added and the reaction mixture is stirred for another hour, after having been heated to 70°C.

EXAMPLE 4

100 g of cellulose in 300 g of isopropanol (87 per cent) are alkalized in a pressure vessel with 56 g of 50 per cent soda lye for 45 minutes at 20°C. Then, 50 g of a 48 per cent aqueous solution of N-methylol acrylamide are added to the alkali cellulose. The material is then reacted for 1 hour at 50°C. After adding 24.8 g of monochloroacetic acid, the temperature is maintained at 70°C for 1 hour. Then, the material is cooled to less than 25°C, and 37.5 ml of ethylene oxide are added. The mixture is then etherified by mixing it for another hour at 70°C. The reaction product obtained is processed as stated above.

EXAMPLE 5

The procedure is as described in Example 1 above, but instead of performing the modification with N-methylol acrylamide dissolved in water, it is carried out with N-(acrylamido methylene)-acetamide dissolved in 87 per cent isobutyl alcohol.

EXAMPLE 6

The procedure is as described in Example 5 above but the modification is performed with N-(acrylamido methylene)-acetamide.

EXAMPLE 7

The procedure is as described in Example 5 above, but the modification is performed with N-(acrylamido methylene)-formamide.

EXAMPLE 8

The procedure is as described in Example 5 above, but the modification is performed with vinyl sulfonamide.

EXAMPLE 9

The procedure is repeated as described in Example 5 above, except that the modification is performed with N-(acrylamido methylene)-amylurethane.

EXAMPLE 10

The procedure is repeated as described in Example 5 above, except that the modification is performed with N-(acrylamido methylene)-methylurethane.

EXAMPLE 11

The procedure is as described in Example 5 above, but the modification is performed with N-(acrylamido carboxymethylene)-ethylurethane.

EXAMPLE 12

The procedure is as described in Example 5 above, but the modification is carried out with N-(acrylamido methylene)-methoxy ethylurethane.

EXAMPLE 13

100 g of cellulose in 100 g of isopropanol (87 per cent) are alkalized with 46 g of 50 per cent soda lye by mixing them for 45 minutes at 20°C. Then, the thus produced alkali cellulose is modified by adding 50 g of a 48 per cent aqueous solution of N-methylol acrylamide and reacting the material for another hour at 50°C, while the mixing is continued. The mixture is then etherified within 1 hour at 70°C, after 55 g of the sodium salt of monochloroacetic acid have been added.

EXAMPLE 14

100 g of cellulose in 300 g of isopropanol (87 per cent) are alkalized with 219 g of 13.7 per cent soda lye by mixing them for 30 minutes at 20°C. The alkali cellulose is then etherified within 1 hour at 70°C, after 75 ml of ethylene oxide have been added. Then, the modification is performed within one hour at 50°C, after 50 g of N-methylol acrylamide (48 per cent) have been added.

| Example No. | Water-retention capacity, in g of water per 100 g of cellulose ether | Water-soluble portion, in per cent by weight |
|---|---|---|
| 1 | 5,940 | 22.0 |
| 2 | 2,460 | 23.7 |
| 3 | 5,970 | 29.7 |
| 4 | 2,010 | 21.8 |
| 5 | 4,540 | 27.4 |
| 6 | 2,100 | 25.4 |
| 7 | 2,800 | 25.3 |
| 8 | 4,630 | 37.7 |
| 9 | 2,460 | 24.8 |
| 10 | 1,540 | 23.6 |
| 11 | 620 | 27.5 |
| 12 | 5,740 | 26.8 |
| 13 | 1,680 | 18.0 |
| 14 | 720 | 19.0 |

It will be obvious to those skilled in the art that many modifications may be made within the scope of the present invention without departing from the spirit thereof, and the invention includes all such modifications.

What is claimed is:

1. In the process for the production of water-adsorbing, but largely water-insoluble, cellulose ethers, in which cellulose is alkalized in the presence of alkali and isopropanol as a reaction medium and is so reacted with an etherification agent that by etherification only a water-soluble cellulose ether is produced, and in which process a modification agent which is able to react with the still free hydroxyl groups of the cellulose anhydro glucose groups in an alkaline reaction medium is reacted before, during, or after the etherification, the improvement which comprises effecting the etherification of cellulose to carboxymethyl cellulose, carboxymethyl hydroxyethyl cellulose, hydroxyethyl cellulose, or methylhydroxyethyl cellulose, reacting with the modification agent in the presence of 0.8 to 7.5 parts by weight of isopropanol, based upon the cellulose weight, and employing a modification agent which has one of the formulae

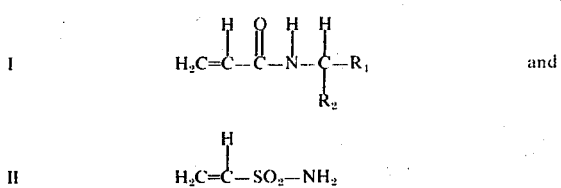

$R_1$ in formula I being hydroxyl, or an acylamino or etherified carbamino group, and $R_2$ in formula I being hydrogen or a carboxyl group.

2. A process according to claim 1 in which the modification agent is N-methylol acrylamide.

3. A process according to claim 1 in which the modification agent is N-(acrylamido methylene)-acetamide.

4. A process according to claim 1 in which the modification agent is N-(acrylamido methylene)-formamide.

5. A process according to claim 1 in which the modification agent is N-(acrylamido methylene)-amylurethane.

6. A process according to claim 1 in which the modification agent is N-(acrylamido methylene)-methylurethane.

7. A process according to claim 1 in which the modification agent is N-(acrylamido carboxy methylene)-ethylurethane.

8. A process according to claim 1 in which the modification agent is N-(acrylamido methylene)-methoxy ethylurethane.

9. A process according to claim 1 in which the modification agent is vinyl sulfonamide.

10. In the process for the production of water-adsorbing, but largely water-insoluble, cellulose ethers, in which cellulose is alkalized in the presence of alkali and isopropanol as a reaction medium and is so reacted with an etherification agent that by etherification only a water-soluble cellulose ether is produced, and in which process a modification agent which is able to react with the still free hydroxyl groups of the cellulose anhydro glucose groups in an alkaline reaction medium is reacted before, during, or after the etherification, the improvement which comprises effecting the etherification of cellulose to carboxymethyl cellulose, carboxymethyl hydroxyethyl cellulose, hydroxyethyl cellulose, or methylhydroxyethyl cellulose, reacting with the modification agent in the presence of 0.8 to 7.5 parts by weight of isopropanol based upon the cellulose weight, and employing a modification agent which is selected from the group consisting of N-methylol acrylamide, N-(acrylamido methylene)-acetamide, N-(acrylamido methylene)-formamide, N-(acrylamido methylene)-amylurethane, N-(acrylamido methylene)-methylurethane, N-(acrylamido carboxy methylene)-ethylurethane, N-(acrylamido methylene)-methoxy ethylurethane, and vinyl sulfonamide.

* * * * *